(12) United States Patent
Tang (10) Patent No.: US 11,849,916 B2
(45) Date of Patent: Dec. 26, 2023

(54) LENS BASE, DISTAL MODULE, ENDOSCOPE, AND ASSEMBLY METHOD FOR DISTAL MODULE

(71) Applicant: HUNAN VATHIN MEDICAL INSTRUMENT CO. LTD., Xiangtan (CN)

(72) Inventor: Peng Tang, Shaoyang (CN)

(73) Assignee: HUNAN VATHIN MEDICAL INSTRUMENT CO. LTD., Xiangtan (CN)

( * ) Notice: Subject to any disclaimer, the term of this patent is extended or adjusted under 35 U.S.C. 154(b) by 0 days.

(21) Appl. No.: 18/057,772

(22) Filed: Nov. 22, 2022

(65) Prior Publication Data
US 2023/0165438 A1   Jun. 1, 2023

(30) Foreign Application Priority Data

Nov. 29, 2021   (CN) .......................... 202111429253.7

(51) Int. Cl.
*A61B 1/00*   (2006.01)
*A61B 1/05*   (2006.01)
*A61B 1/06*   (2006.01)

(52) U.S. Cl.
CPC ...... *A61B 1/00071* (2013.01); *A61B 1/00131* (2013.01); *A61B 1/05* (2013.01); *A61B 1/0676* (2013.01)

(58) Field of Classification Search
CPC .............. A61B 1/00071; A61B 1/0008; A61B 1/00096; A61B 1/00131; A61B 1/05; A61B 1/06; A61B 1/0676
See application file for complete search history.

(56) References Cited

U.S. PATENT DOCUMENTS

| 6,447,445 B1 | 9/2002 | Hirano | |
| 2005/0075538 A1* | 4/2005 | Banik | A61B 1/0016 600/152 |
| 2014/0330081 A1* | 11/2014 | Imai | A61B 1/0008 600/129 |

(Continued)

FOREIGN PATENT DOCUMENTS

| CN | 107822580 A | 3/2018 |
| CN | 208724089 U | 4/2019 |
| CN | 212394877 U | 1/2021 |

(Continued)

*Primary Examiner* — Aaron B Fairchild
(74) *Attorney, Agent, or Firm* — Bayramoglu Law Offices LLC (57) ABSTRACT

A lens base, a distal module, an endoscope, and an assembly method for the distal module are provided. The lens base includes a lens base body, where the lens base body is axially provided with a camera module accommodating portion that includes a camera channel and an illumination channel. A side wall of the lens base body is provided with a camera module opening portion. The camera module opening portion includes a first opening portion and a second opening portion that are adjacent to each other. The first opening portion is communicated with the camera channel, and the second opening portion is communicated with the illumination channel. The first opening portion is configured to mount a camera unit, and the second opening portion is configured to mount an illumination unit.

12 Claims, 7 Drawing Sheets

(56) References Cited

U.S. PATENT DOCUMENTS

2020/0297191 A1    9/2020    Krivopisk et al.

FOREIGN PATENT DOCUMENTS

| CN | 213429984 U | 6/2021 |
|---|---|---|
| JP | H03101903 U | 10/1991 |
| JP | 2004290492 A | 10/2004 |
| JP | 2019013665 A | 1/2019 |
| WO | 2013035379 A1 | 3/2013 |
| WO | 2016121505 A1 | 8/2016 |

* cited by examiner

LENS BASE, DISTAL MODULE, ENDOSCOPE, AND ASSEMBLY METHOD FOR DISTAL MODULE

CROSS REFERENCE TO THE RELATED APPLICATIONS

This application is based upon and claims priority to Chinese Patent Application No. 202111429253.7, filed on Nov. 29, 2021, the entire contents of which are incorporated herein by reference.

TECHNICAL FIELD

The present disclosure relates to the technical field of endoscopes and in particular to a lens base, a distal module, an endoscope, and an assembly method for the distal module.

BACKGROUND

The endoscope is a common medical device composed of a bendable part, a light source, and a set of lenses. The endoscope enters the human body through a natural lumen or a small surgical incision of the human body. When in use, the endoscope is introduced into a pre-examined organ to directly observe the changes in the relevant part. Image quality directly affects the use effect of the endoscope and also indicates the development level of the endoscopy. The earliest endoscope was used for rectal examination, where the doctor inserted a hard tube into the patient's anus and observed rectal lesions with the help of the light of a candle. The examination was unable to acquire abundant diagnostic data, painful for the patient, and easy to cause a puncture due to the hard feature of device. With the continuous development and application of endoscopy to address these defects, different types of endoscopes have been designed for different purposes.

In the prior art, the camera unit and the illumination unit for photographing and illuminating the viewing zone of the endoscope are arranged at the distal end of the endoscope.

In the endoscope disclosed by Chinese patent application CN208724089U, the photoelectric coupler and the light-emitting diode (LED) light source are integrated through a protective sleeve and fixed and sealed with glue. The endoscope uses both transparent glue and black glue. The transparent glue is provided between the LED light source and the protective sleeve, and the black glue is provided between the photoelectric coupler, the wire, and the protective sleeve. However, the transparent glue covers the photoelectric coupler, and the light will be refracted when passing through the transparent glue, thereby affecting image acquisition.

Due to the small size of the distal end of the endoscope, a space-saving design is needed to accommodate all the required components in the limited space. During assembly, the illumination unit and the camera unit are inserted into the narrow space from the rear end to the front end, which is very difficult to assemble, and easily causes damage to the illumination unit and the camera unit.

SUMMARY

An objective of the present disclosure is to provide a lens base, a distal module, an endoscope, and an assembly method for the distal module, which facilitates the mounting of a camera unit and an illumination unit and avoids damaging the camera unit and the illumination unit.

A first aspect of the present disclosure provides a lens base. The lens base includes a lens base body, where the lens base body is axially provided with a camera module accommodating portion that includes a camera channel and an illumination channel.

A side wall of the lens base body is provided with a camera module opening portion; the camera module opening portion includes a first opening portion and a second opening portion that are adjacent to each other. The first opening portion is communicated with the camera channel, and the second opening portion is communicated with the illumination channel. The first opening portion is configured to mount a camera unit, and the second opening portion is configured to mount an illumination unit.

Further, the first opening portion and the second opening portion are partially identical in terms of open direction.

Further, the lens base includes an operation channel, and a side wall of the operation channel facing the lens base body is provided with a third opening portion that is configured to mount an operation tube.

Further, the lens base body is made of a transparent material, and the side wall of the illumination channel is coated with a light shielding layer.

A second aspect of the present disclosure provides a distal module, including a camera module and the above lens base, where the camera module is at least partially accommodated in the camera module accommodating portion.

The camera module includes a camera unit, an illumination unit, and a support unit. The camera unit and the illumination unit are arranged on the same side of the support unit. The camera unit, the illumination unit, and the support unit are integrally arranged.

Further, the distal module includes a sleeve sleeved on the peripheral wall of the lens base.

Further, the distal module includes a lens covering the top outlet of the camera channel.

Further, the top end of the illumination unit is lower than the front end of the lens base.

A third aspect of the present disclosure provides an endoscope, which includes a handle portion and an insertion portion. The insertion portion includes a bending portion and the above distal module, and the bending portion is fixedly connected to the distal module.

A fourth aspect of the present disclosure provides an assembly method for the distal module, including the following steps:

S10: mounting the camera module into the camera module accommodating portion from the camera module opening portion and S20: sleeving the lens base sleeve on the peripheral wall of the lens base.

To sum up, the present disclosure has the following technical features:

1. The present disclosure provides the lens base, which facilitates the mounting of the camera module, and effectively avoids damaging the illumination unit and the camera unit during assembly.

2. The present disclosure provides the camera module accommodating portion axially on the lens base body and the camera module opening portion on the side wall of the lens base body. The design facilitates the mounting of the camera module into the lens base body from the side and avoids damaging the camera module.

3. The present disclosure provides the first opening portion communicated with the camera channel and the second opening portion communicated with the illumination channel, such that the camera unit and the illumination unit are mounted into the camera channel and the illumination channel respectively from the side, which facilitates the mounting and positioning of the integrated camera module.

4. The present disclosure coats a light shielding layer on the side wall of the illumination channel when the lens base body is made of a transparent material. The design further prevents the light of the illumination unit from penetrating the lens base of the endoscope to avoid the influence of light refraction on image acquisition, thereby improving the image acquisition quality.

BRIEF DESCRIPTION OF THE DRAWINGS

To describe the technical solutions in the embodiments of the disclosure more clearly, the following briefly introduces the drawings required for describing the embodiments or the prior art. It will become apparent that the drawings in the following description show merely some embodiments of the disclosure, and persons of ordinary skill in the art may still derive other drawings from these drawings without creative efforts.

Reference Numerals: 100. lens base; 110. lens base body; 120. operation channel; 121. third opening portion; 130. camera channel; 131. first opening portion; 140. illumination channel; 141. second opening portion; 200. distal module; 210. camera module; 211. camera unit; 212. illumination unit; 213. support unit; 220. sleeve; 230. lens; 310. bending portion; and 320. operation tube.

DETAILED DESCRIPTION OF THE EMBODIMENTS

The following description provides many different embodiments or examples for implementing different features of the present disclosure. The elements and arrangements described in the following specific examples are only intended to concisely express the present disclosure and are only for illustration purposes, rather than to limit the present disclosure.

In the description of the present disclosure, it should be understood that orientation or position relationships indicated by terms such as "upper", "lower", "front", "rear", "left", "right", "vertical", "horizontal", "top", "bottom", "inside", and "outside" is based on what is illustrated in the drawings. These terms are merely intended to facilitate and simplify the description of the present disclosure, rather than to indicate or imply that the mentioned device or components must have a specific orientation or must be constructed and operated in the specific orientation. Therefore, these terms should not be understood as a limitation of the present disclosure. In addition, the terms such as "first" and "second" are used only for descriptive purposes and should not be construed as indicating or implying relative importance or implying the number of indicated technical features. Therefore, the features defined by "first" and "second" can explicitly or implicitly include one or more features. In the description of the present disclosure, "multiple" means two or more, unless otherwise specifically defined.

In the description of the present disclosure, it should be noted that unless otherwise expressly specified, terms such as "mounted", "connected to", and "connected with" should be comprehended in a broad sense. For example, the "connection" may be a fixed connection, a removable connection, or an integral connection; a mechanical connection, an electrical connection, or mutual communication; a direct connection or an indirect connection via an intermediate medium, or an interconnection or an interaction relationship between two elements. Those of ordinary skill in the art may understand specific meanings of the above terms in the present disclosure based on a specific situation.

In the present disclosure, unless otherwise expressly specified, when it is described that a first feature is "above" or "under" a second feature, it may indicate that the first feature is in direct contact with the second feature, or that the first feature and the second feature are not in direct contact with each other but are in contact via another feature between them. In addition, when it is described that the first feature is "over", "above", and "on" the second feature, it may indicate that the first feature is directly above and diagonally above the second feature or simply indicate that the height of the first feature is larger than that of the second feature. When it is described that the first feature is "beneath", "below", and "under" the second feature, it may indicate that the first feature is directly below and diagonally below the second feature or simply indicate that the height of the first feature is smaller than that of the second feature.

In addition, reference numerals and/or reference letters may be repeated in different examples in the present disclosure, and such repetition is for purposes of simplification and clarity and is not indicative of relationships between the implementations and/or settings discussed. In addition, while the present disclosure provides examples of various specific processes and materials, those of ordinary skill in the art may be aware of applications of other processes and/or uses of other materials.

The preferred embodiments of the present disclosure are described below by referring to the drawings. It should be understood that the preferred embodiments described herein are only used to illustrate the present disclosure, rather than to limit the present disclosure.

Embodiment 1

Embodiment 1 of the present disclosure provides lens base 100. The lens base includes lens base body 110. The lens base body is axially provided with a camera module accommodating portion that includes camera channel 130 and illumination channel 140.

A side wall of the lens base body 110 is provided with a camera module opening portion. The camera module opening portion includes first opening portion 131 and second opening portion 141 which are adjacent to each other. The first opening portion 131 is communicated with the camera channel 130, and the second opening portion 141 is communicated with the illumination channel 140. The first opening portion 131 is configured to mount a camera unit, and the second opening portion 141 is configured to mount an illumination unit.

This embodiment does not limit the material of the lens base body 110, which can be either transparent or opaque.

This embodiment provides the lens base 100, which facilitates the mounting of the camera module, and effectively avoids damaging the illumination unit and the camera unit during assembly.

This embodiment provides the camera module accommodating portion axially on the lens base body 110 and the camera module opening portion on the side wall of the lens base body. The design facilitates the mounting of the camera module into the lens base body from the side and avoids damaging the camera module.

This embodiment provides the first opening portion 131 communicated with the camera channel and the second opening portion 141 communicated with the illumination channel, such that the camera unit and the illumination unit are mounted into the camera channel and the illumination channel respectively from the side, which facilitates the mounting and positioning of the integrated camera module.

Further, the first opening portion 131 and the second opening portion 141 are partially identical in terms of open direction.

Figure 1:
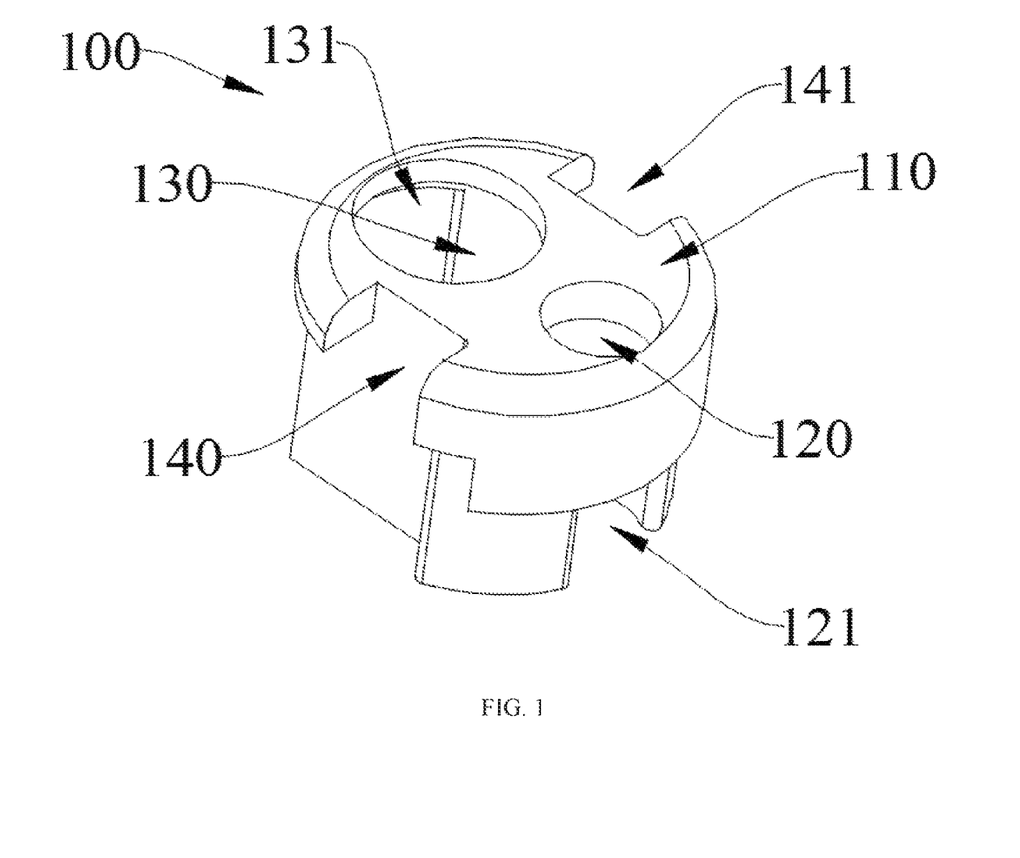
FIG. 1 is a stereoscopic view of a lens base according to the present disclosure.
Figure 2:
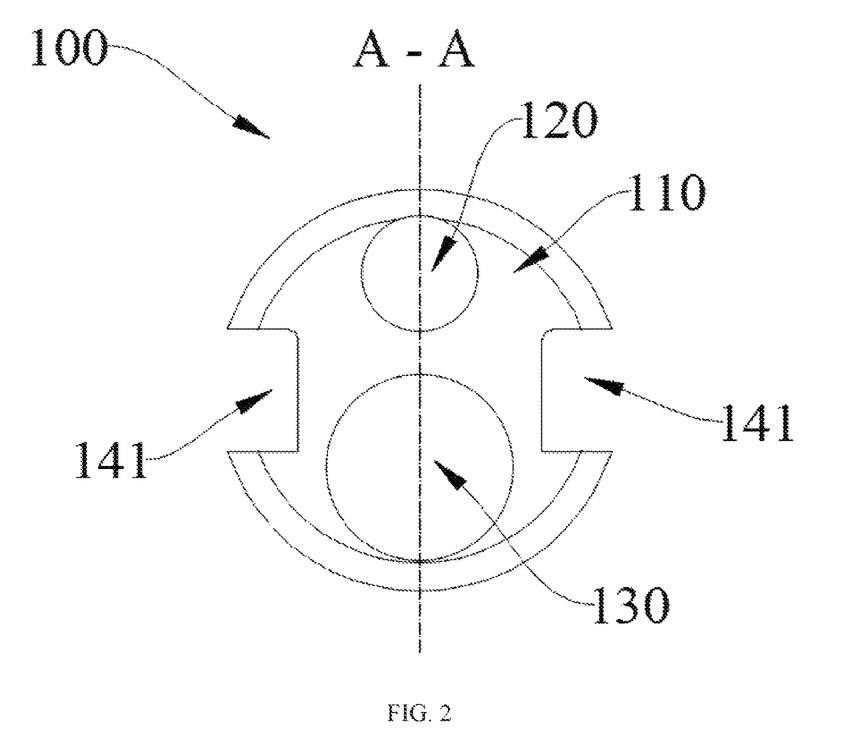
FIG. 2 is a top view of the lens base according to the present disclosure.
Figure 3:
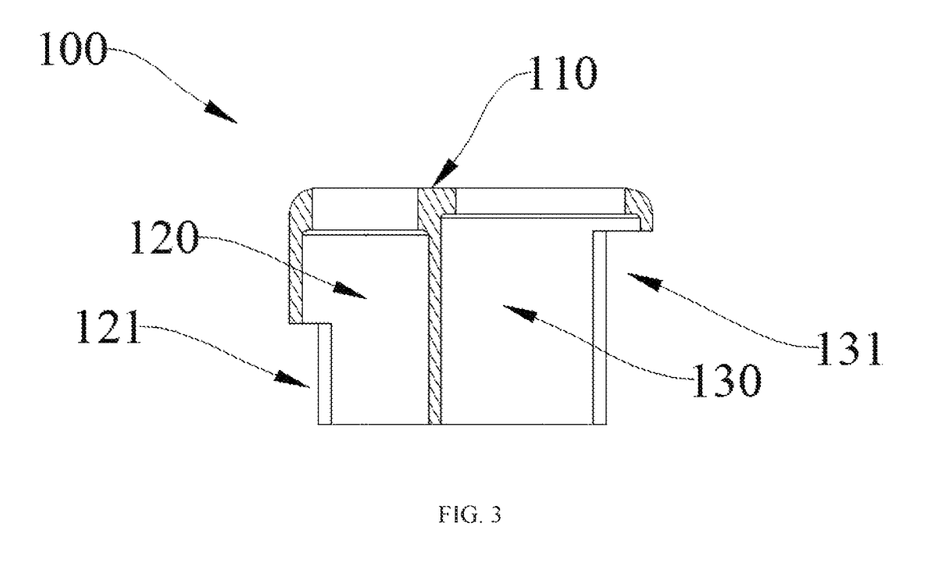
FIG. 3 is a sectional view of the lens base along line A-A as shown in FIG. 2 according to the present disclosure.
Figure 4:
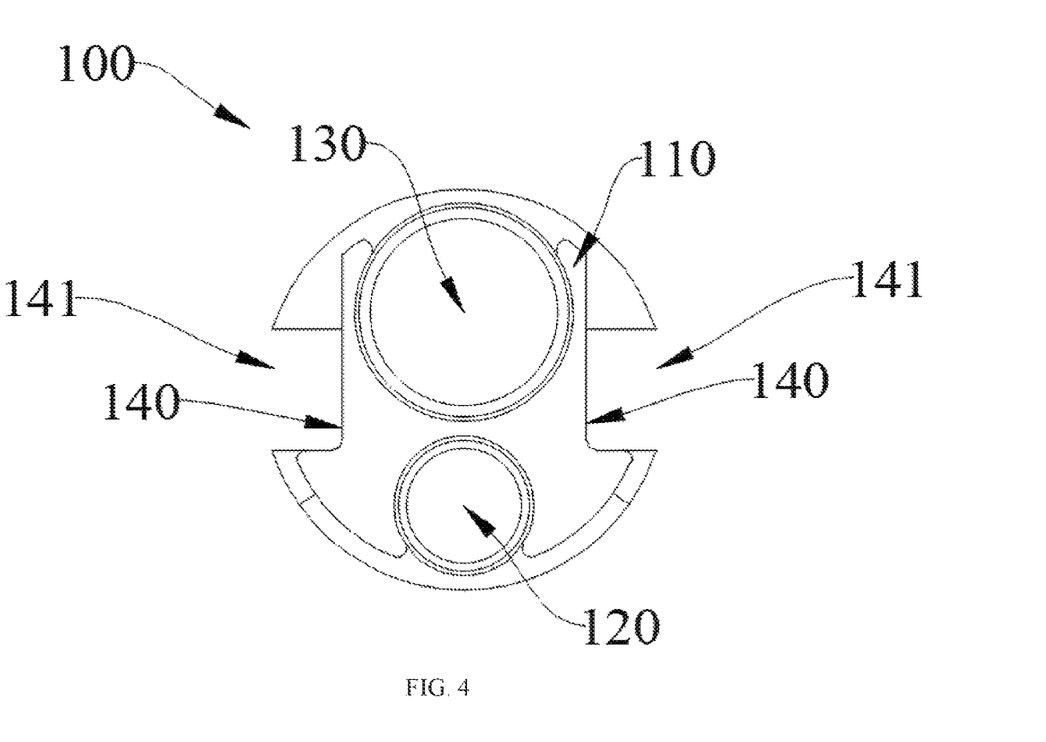
FIG. 4 is a bottom view of the lens base according to the present disclosure.
Figure 5:
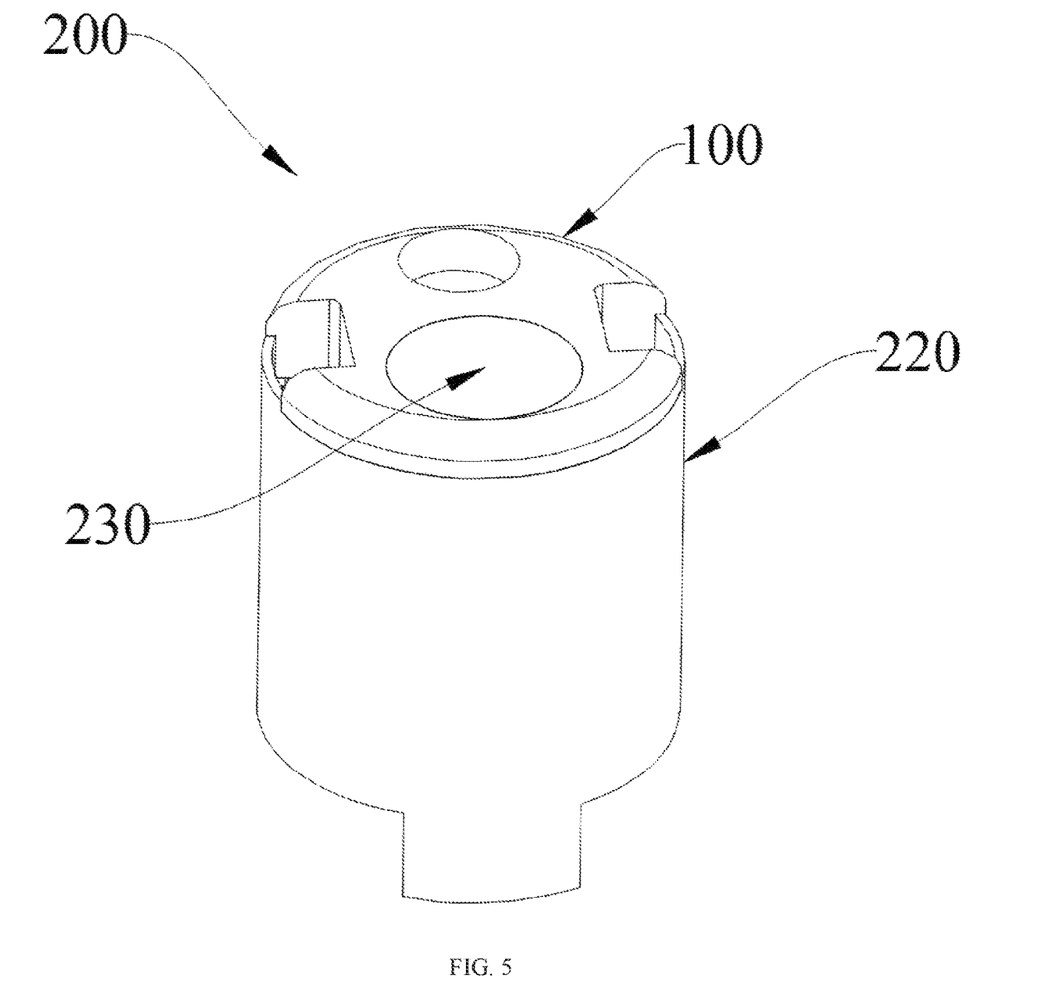
FIG. 5 is a stereoscopic view of a distal module according to the present disclosure.
Figure 6:
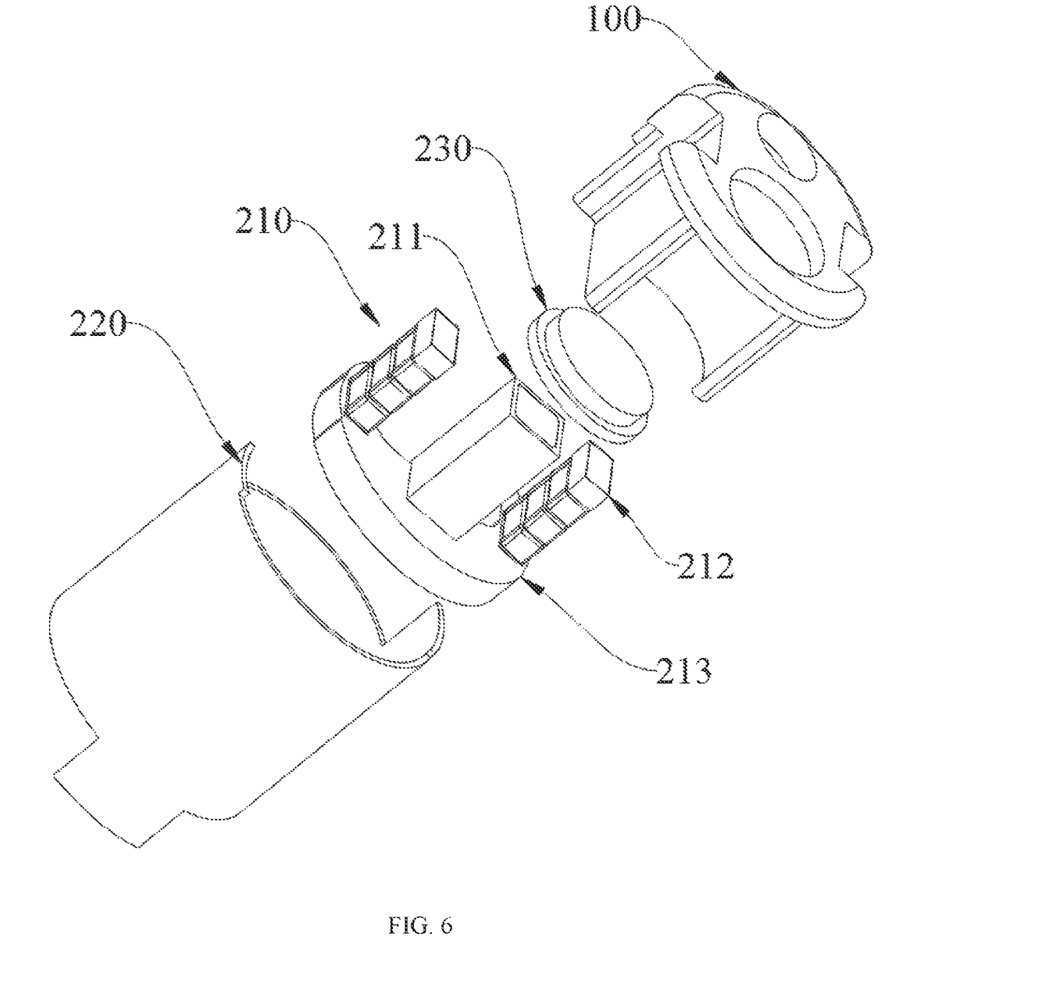
FIG. 6 is an exploded view of the distal module according to the present disclosure.
Figure 7:
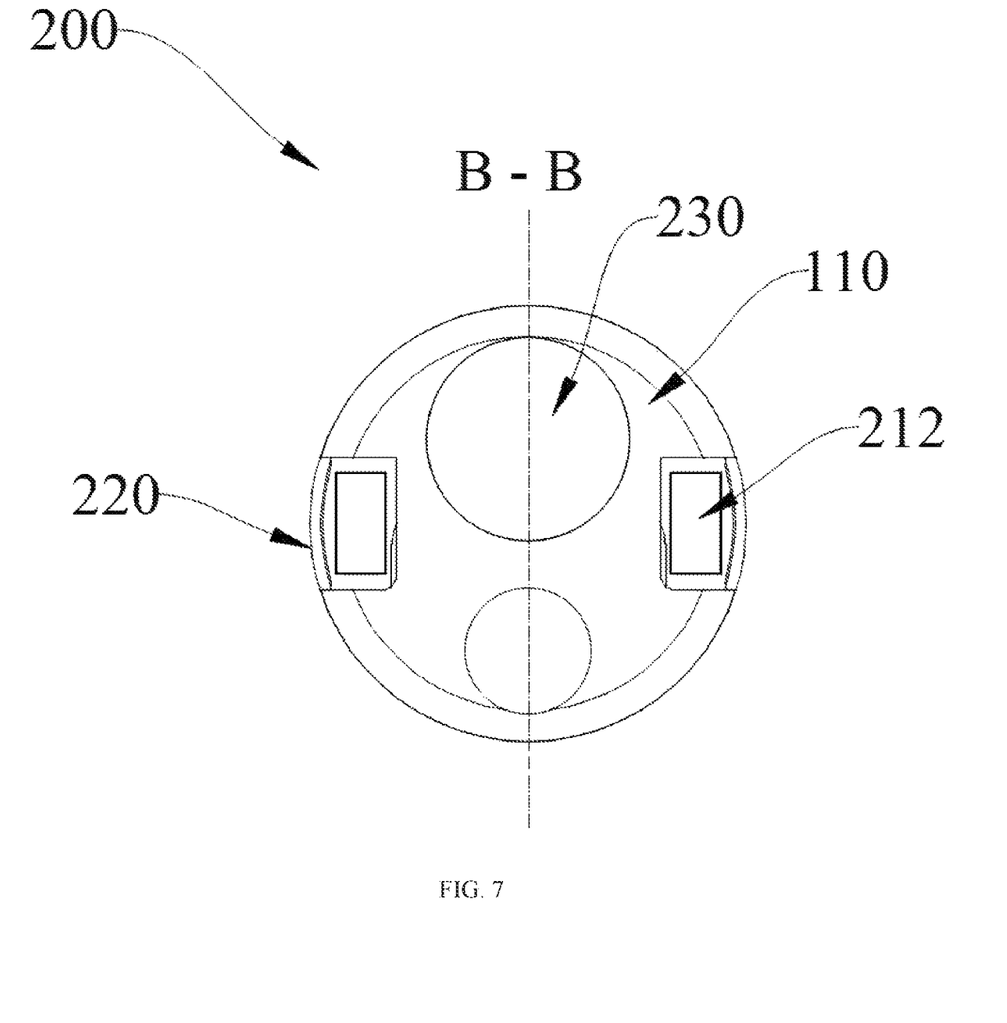
FIG. 7 is a top view of the distal module according to the present disclosure.
Figure 8:
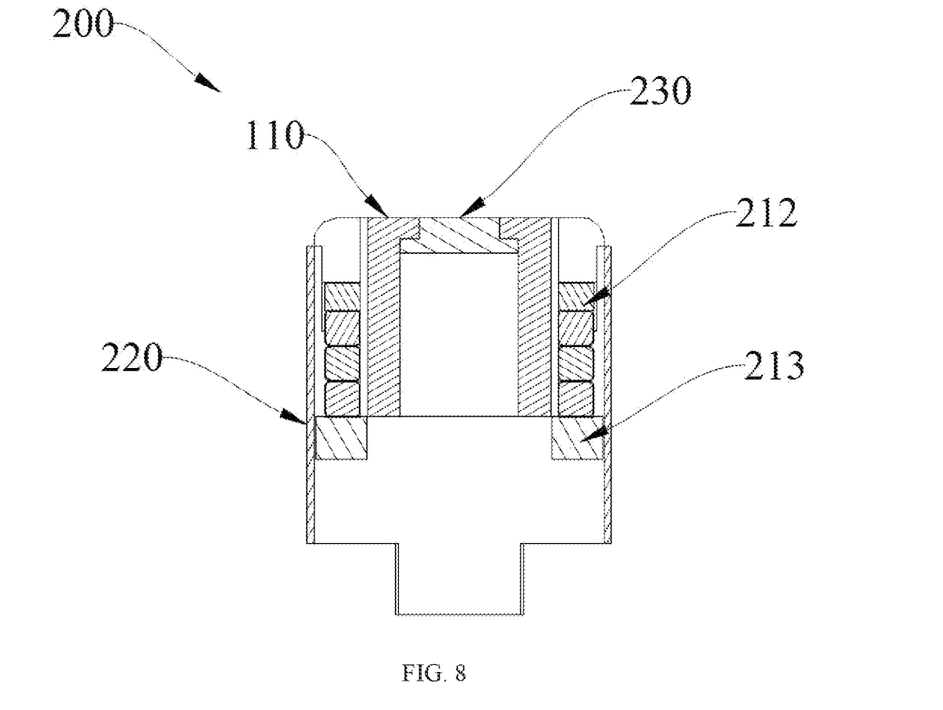
FIG. 8 is a sectional view of the distal module along line B-B as shown in FIG. 7 according to the present disclosure.

As shown in FIG. 4, the first opening portion that communicates with the camera channel 130 and the second opening portion that communicates with the illumination channel 140 are both provided with openings facing upward. The design allows the camera module to be mounted from the same side and further improves the mounting efficiency when the camera module is an integrated structure.

Meanwhile, the open direction of the second opening portion communicated with the illumination channel 140 extends to an adjacent direction to form a left opening and/or a right opening, as shown in FIG. 4. The design is easy for the relevant personnel to fix and adjust the illumination unit mounted in the illumination channel, thereby realizing the positioning and accurate mounting of the camera module.

Further, the lens base includes operation channel 120. A side wall of the operation channel 120 facing the lens base body 110 is provided with third opening portion 121. The third opening portion 121 is configured to mount operation tube 320.

The operation channel 120 is configured to mount the operation tube 320, and the operation tube 320 is configured to allow the passage of operating instruments such as scalpels and forceps, as well as liquid media like medicine or water.

A side wall of the operation channel 120 is provided with a recessed portion. The recessed portion is fitted with an outer wall of the operation tube 320. An end of the operation tube 320 is lower than the front end of the operation channel 120. The recessed portion enhances the fixation and sealing of the operation tube 320.

Further, the lens base body 110 is made of a transparent material, and the side wall of the illumination channel 130 is coated with a light shielding layer.

This embodiment coats a light shielding layer on the side wall of the illumination channel when the lens base body is made of a transparent material. The design further prevents the light of the illumination unit from penetrating the lens base of the endoscope to avoid the influence of light refraction on image acquisition, thereby improving the image acquisition quality.

Embodiment 2

Embodiment 2 of the present disclosure provides distal module 200, including camera module 210 and lens base 100. The camera module 210 is at least partially accommodated in the camera module accommodating portion.

The camera module 210 includes camera unit 211, illumination unit 212, and support unit 213. The camera unit 211 and the illumination unit 212 are arranged on the same side of the support unit 213; the camera unit 211, the illumination unit 212, and the support unit 213 are integrally arranged.

This embodiment allows the integrated camera module to be mounted into the lens base body from the side to avoid damage and effectively improve the success rate and assembly efficiency of the distal module 200.

Further, the distal module includes sleeve 220. The sleeve 220 is sleeved on a peripheral wall of the lens base 100. The sleeve 220 is configured to fix the lens base 100 and the camera module 210 and is connected to another structure of the endoscope.

Further, the distal module includes a lens 230. The lens 230 covers the top outlet of the camera channel 130. The lens 230 is configured to protect the camera unit and prolong the service life of the camera unit. The lens 230 may be provided with a camera sleeve positioning portion.

Further, the top end of the illumination unit 212 is lower than the front end of the lens base 100.

This embodiment makes the top end of the illumination unit 212 lower than the front end of the lens base 100 to prevent the light emitted by the illumination unit from being refracted into a camera, thereby preventing the image from showing blue light or being unclear.

Embodiment 3

Figure 9:
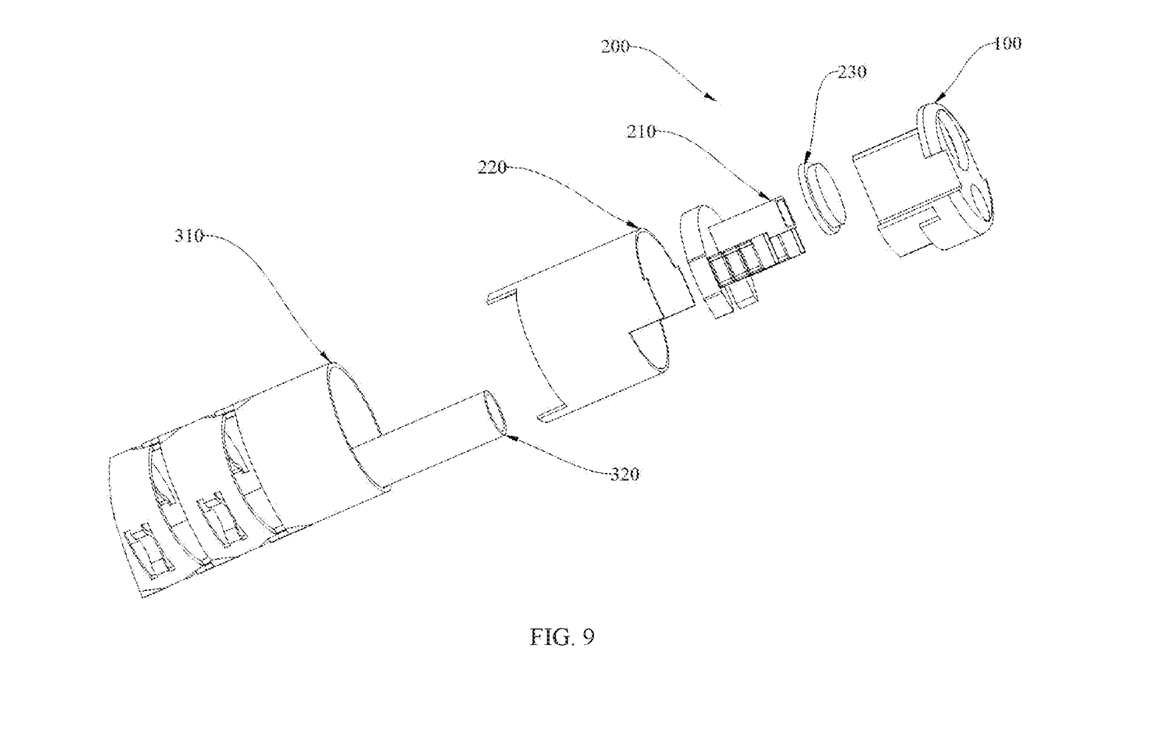
FIG. 9 is a partial view of an endoscope according to the present disclosure.

Embodiment 3 of the present disclosure provides an endoscope, which includes a handle portion and an insertion portion. The insertion portion includes bending portion 310 and distal module 200. The bending portion 310 is fixedly connected to the distal module 200.

The handle portion and the insertion portion composed of the bending portion 310 and the distal module 200 form the endoscope for the examination of internal organs. The endoscope may further be provided therein with an operation tube 320, through which sampling or medium flow can be achieved for the purpose of sampling or treatment.

Embodiment 4

Embodiment 4 of the present disclosure provides an assembly method for the distal module, including the following steps:

S10. Camera module 210 is mounted into a camera module accommodating portion from a camera module opening portion.

S20. Lens base sleeve 220 is sleeved on the peripheral wall of lens base 100.

This embodiment mounts the camera module 210 into the camera module accommodating portion from the camera module opening portion on the side wall of the lens base body, thereby mounting the camera module 210 from the side of the lens base body. This design effectively solves the problem of difficult assembly in a narrow space, effectively avoids damage to the illumination unit and the camera unit during assembly, and has positive practical significance in the industrial application field.

The above described are merely preferred embodiments of the present disclosure and are not intended to limit the present disclosure. Any modifications, equivalent replacements, and improvements made within the spirit and principle of the present disclosure should all fall within the scope of protection of the present disclosure.

What is claimed is:

1. A distal module, comprising:
a camera module and lens base;
the camera module comprising a camera unit, an illumination unit, and a support unit, the camera unit and the illumination unit are arranged on the same side of the support unit;
the camera unit, the illumination unit and the support unit are integrally arranged;
the lens base comprising a lens base body made of a transparent material;
the lens base body comprising a side wall, a camera module accommodating portion, and a camera module opening portion;
wherein the lens base body is axially provided with the camera module accommodating portion, and the camera module accommodating portion comprises a camera channel and an illumination channel, a side wall of the illumination channel coated with a light shielding layer;
the side wall of the lens base body is provided with the camera module opening portion;
the camera module opening portion comprises a first opening portion and a second opening portion;
the first opening portion and the second opening portion are located on the side wall and are adjacent to each other, wherein the first opening portion is connected with the camera channel and the second opening portion is connected with the illumination channel;
the first opening portion is configured to mount the camera unit into the camera channel;
the second opening portion is configured to mount the illumination unit into the illumination channel;
wherein the camera module is at least partially accommodated in the camera module accommodating portion; and
wherein the illumination unit is contained inside the lens base body and is located at a distance away from a front surface of the lens base body.

2. The distal module according to claim 1, wherein the distal module further comprises:
a sleeve, and the sleeve is sleeved on a peripheral wall of the lens base.

3. The distal module according to claim 1, wherein the distal module further comprises:
a lens, wherein the lens covers an outlet of the camera channel.

4. An endoscope, comprising:
a handle portion and an insertion portion,
wherein the insertion portion comprises a bending portion and the distal module according to claim 1; and
the bending portion is fixedly connected to the distal nodule.

5. The endoscope according to claim 4, wherein t further comprises:
a sleeve, and the sleeve is sleeved on a peripheral wall of the lens base.

6. The endoscope according to claim 4, wherein the distal module further comprises:
a lens, wherein the lens covers an outlet of the camera channel.

7. The endoscope according to claim 4, wherein in the distal module, the illumination unit is contained inside the lens base body and is located at a distance away from a front surface of the lens base body.

8. An assembly method for the distal module according to claim 1, comprising the following steps:
S10: mounting the camera module into the camera module accommodating portion from the camera module opening portion; and
S20: sleeving the lens base sleeve on a peripheral wall of the lens base.

9. The assembly method according to claim 8, wherein the distal module further comprises:
a sleeve, and the sleeve is sleeved on the peripheral wall of the lens base.

10. The assembly method according to claim 8, wherein the distal module further comprises:
a lens, wherein the lens covers an outlet of the camera channel.

11. The assembly method according to claim 8, wherein in the distal module, the illumination unit is contained inside the lens base body and is located at a distance away from a front surface of the lens base body.

12. The distal module according to claim 1, wherein
the lens base further comprises an operation channel;
a side wall of the operation channel facing the lens base body is provided with a third, opening portion; and
the third opening portion is configured to mount an operation tube.

* * * * *